US009430098B2

(12) United States Patent
Lazarescu et al.

(10) Patent No.: US 9,430,098 B2
(45) Date of Patent: Aug. 30, 2016

(54) FREQUENCY SENSING AND MAGNIFICATION OF PORTABLE DEVICE OUTPUT

(71) Applicant: Apple Inc., Cupertino, CA (US)

(72) Inventors: Paul Orri Lazarescu, Irvine, CA (US); Daniel Goodman, Greenbrae, CA (US); Adithya Raghavan, Los Altos, CA (US)

(73) Assignee: APPLE INC., Cupertino, CA (US)

( * ) Notice: Subject to any disclaimer, the term of this patent is extended or adjusted under 35 U.S.C. 154(b) by 279 days.

(21) Appl. No.: 13/717,693

(22) Filed: Dec. 17, 2012

(65) Prior Publication Data

US 2014/0168170 A1 Jun. 19, 2014

(51) Int. Cl.
*G06F 3/043* (2006.01)
*G01H 13/00* (2006.01)
*G01N 29/12* (2006.01)
*G01H 1/00* (2006.01)

(52) U.S. Cl.
CPC .............. *G06F 3/043* (2013.01); *G01H 1/00* (2013.01); *G01H 13/00* (2013.01); *G01N 29/12* (2013.01); *G01N 2291/028* (2013.01); *G01N 2291/02854* (2013.01)

(58) Field of Classification Search
CPC ........................................................ G06F 3/043
USPC ........................................ 345/169, 173, 179
See application file for complete search history.

(56) References Cited

U.S. PATENT DOCUMENTS

| 7,345,677 | B2* | 3/2008 | Ing et al. ....................... 345/173 |
| 8,477,463 | B2* | 7/2013 | Ms .................................... 361/20 |
| 2004/0239651 | A1* | 12/2004 | Sakurai ......................... 345/179 |
| 2009/0243997 | A1* | 10/2009 | Tierling et al. ............... 345/156 |
| 2009/0273583 | A1* | 11/2009 | Norhammar ................. 345/177 |
| 2010/0164869 | A1* | 7/2010 | Huang et al. ................ 345/168 |
| 2011/0191680 | A1* | 8/2011 | Chae et al. ................... 715/716 |
| 2012/0035934 | A1* | 2/2012 | Cunningham ............... 704/260 |
| 2012/0120014 | A1* | 5/2012 | Nikolovski et al. .......... 345/173 |
| 2012/0274609 | A1* | 11/2012 | Sheng et al. ................. 345/177 |
| 2012/0302293 | A1* | 11/2012 | Johnson et al. .............. 455/567 |

* cited by examiner

*Primary Examiner* — Kumar Patel
*Assistant Examiner* — Afroza Chowdhury
(74) *Attorney, Agent, or Firm* — Brownstein Hyatt Farber Schreck, LLP

(57) ABSTRACT

Devices, using emitted acoustic signals and received vibrations, determine resonant frequencies of a surface or other object, and determine useful information about that surface, including size, thickness, and material. Received vibrations include impulse vibrations from striking that surface with a finger or stylus, or from a frequency or from a swept-sinusoid emitted by the device. The device can adjust its frequency output to use the surface as an amplifier for alarms or speakers, or a center frequency for sonic output. Using an accelerometer, devices sense impulse vibrations, translating those impulses into information, such as keystrokes, game controls, mice, or musical instrument controls. Devices can emulate keyboards and input devices using tabletops. Devices can coordinate signals through multiple media, including air, surface, or EMF channels.

29 Claims, 6 Drawing Sheets

FREQUENCY SENSING AND MAGNIFICATION OF PORTABLE DEVICE OUTPUT

TECHNICAL FIELD

This application relates to an iPhone frequency sensor/magnifier application, and other matters.

BACKGROUND

Many physical objects, particularly those having defined surfaces that are relatively wider than they are thick, are characterized by a resonant frequency, that is, a frequency at which those physical objects exhibit a maximum (or at least a local maximum) energy response to vibrations. For example, a wooden tabletop might, depending on its size, thickness, and the substance from which it is made, have a particular frequency at which it might vibrate, and at which it might amplify vibrations if those vibrations are applied to that tabletop at that frequency.

This can have the effect that a speaker, or a speaker in combination with an amplifier, can deliberately cause the tabletop to vibrate at a relative maximum, by emitting vibrations (such as sound) that match the resonant frequency of that tabletop.

This can also have the effect that a sensor, or a sensor in combination with an amplifier, can detect or otherwise determine the resonant frequency of a tabletop on which it sits, in response to vibrations of the tabletop and in response to whether that sensor detects relative amplification or relative damping of those vibrations.

BRIEF DESCRIPTION OF THE DISCLOSURE

This application provides techniques, including devices and methods, which can determine a resonant frequency and possibly other characteristics of the object. For example, devices and methods as described herein can determine a resonant frequency of a surface upon which a frequency device (as described herein) is placed, and can in response thereto, determine useful information about that surface, such as its size, thickness, and construction materials included in that surface.

In one embodiment, one or more devices as described herein can emit one or more selected frequencies, and can detect a response of an object to which the devices are coupled, such as when the devices are placed upon a surface of the object. In response to this information, the devices can determine useful information about the object. The device can adjust its operation in response to information about the object, which can have the effect of improving performance of the device in one or more characteristics. For example, a speaker can emit vibrations at one or more known frequencies and can, in response to whether the tabletop amplifies or dampens vibrations at those frequencies, determine whether those frequencies include one or more resonant frequencies of the tabletop. In response to the resonant frequencies of the tabletop, the speaker can use the tabletop as an alarm or speaker, or as a center frequency for sonic output (such as a center frequency for playing music).

This application provides techniques, including devices and methods, which can sense acoustic vibrations from an object, such as received from a finger or stylus applied to the object, from a frequency emitted by a device applied to the object, or from a swept-sinusoid signal emitted by a device applied to the object. For example, devices and methods as described herein can sense impulse vibrations from an object coupled to a device having an inertial response sensor, and can in response thereto, determine useful information about those vibrations, such as their duration, location, volume, and materials used to induce those vibrations.

In one embodiment, one or more devices as described herein can receive one or more impulse vibrations from an object, such as using an accelerometer or another inertial response sensor (such as a gyroscope or otherwise), and can translate those impulse vibrations into information, such as a direction or location from which the vibrations originate, or a number of those vibrations that are received. The device can adjust its operation in response to the vibrations, such as constructing input data for the device. For example, devices can receive impulse vibrations or other vibrations from one or more locations on a tabletop, and can, in response to a measure of how much the tabletop amplifies or dampens vibrations from those locations, emulate a keyboard, keypad, mouse or trackpad, game controller, musical instrument control, or other input for a computing device.

This application provides techniques, including methods and systems, which can coordinate devices, such as having at least one emitter and at least one sensor, and coupled using one or more radio frequency (RF) or other electromagnetic frequency (EMF) channels. For example, methods and systems as described herein can emit vibrations from a first device and receive vibrations at a second device, the first device sending those vibrations to the second device both using (a) EMF techniques, such as using Bluetooth™ or radiotelephone techniques, near field communication, or otherwise; as well as (b) sonic techniques deliberately mediated by the resonant frequency of one or more objects to which the first and second device are coupled.

In one embodiment, the first and second device can each include a cellular telephone, such as an iPhone™ or other device, wherein the first and second device can be disposed to communicate using EMF techniques, such as a cellular telephone circuit or a packet switched network. In alternative embodiments, the first and second device can each include other devices disposed to communicate using EMF techniques, such as other cellular telephones, an iPad™ or other computing tablet, a netbook, a laptop computer or other portable personal computer, or otherwise. The first and second device can each be disposed on a tabletop, such as a wooden tabletop disposed to support both the first and second device, and disposed to transmit an acoustic signal from the first to the second device. The first device can be disposed to emit one or more such acoustic signals, such as a known frequency for which a frequency response from the tabletop is known to at least either the first or second device, and the second device can be disposed to receive those acoustic signals, such as mediated by that frequency response from the tabletop. The first and second device can be disposed to compare the emitted acoustic signal with the received acoustic signal, in response to which one or both of them can determine an impulse response or a resonant frequency of the tabletop.

While multiple embodiments are disclosed, including variations thereof, still other embodiments of the present disclosure will become apparent to those skilled in the art from the following detailed description, which shows and describes illustrative embodiments of the disclosure. As will be realized, the disclosure is capable of modifications in various obvious aspects, all without departing from the spirit and scope of the present disclosure. Accordingly, the drawings and detailed description are to be regarded as illustrative in nature and not restrictive.

DETAILED DESCRIPTION

Terminology

The following terminology is exemplary, and not intended to be limiting in any way.

The text "frequency device", and variants thereof, generally refers to any device capable of generating a sound or other vibration, such as a mobile sound player, mobile telephone, iPhone™, or otherwise. For example, a frequency device can include another type of cellular telephone, an iPod™ or other mobile media player, such as an MP3 player or other music player, an iPad™ or other computing tablet, a netbook, a laptop computer or other portable personal computer, or otherwise. The amount of sound or vibration need not be concentrated in any particular frequency band, and need not be confined to any particular frequency band, such as a human audible frequency band. For some examples, the frequency band can be a human audible frequency band, or another frequency band such as an infrasonic or ultrasonic frequency band. Moreover, the amount of sound or vibration need not be constant, or periodic, or follow any particular pattern.

The text "resonant surface", "surface", and variants thereof, generally refers to any surface, or any other portion of an object, whether solid or otherwise, having at least one definable frequency at which that resonant surface has (at least a local) maximum in its response to a frequency applied to that resonant surface. For some examples, a resonant surface can include a relatively flat surface including metal, plastic, wood, or combinations or composites thereof, such as having the effect that a particular frequency is received by the resonant surface and amplified relative to other frequencies. In one such case, a tabletop can have the property that it might reverberate more loudly at 1 KHz than at other frequencies, in which case the 1 KHz frequency would be said to be a resonant frequency of that resonant surface.

After reading this application, those skilled in the art would recognize that these statements of terminology would be applicable to techniques, methods, physical elements, and systems (whether currently known or otherwise), including extensions thereof inferred or inferable by those skilled in the art after reading this application.

Frequency Device on a Surface

Figure 1:
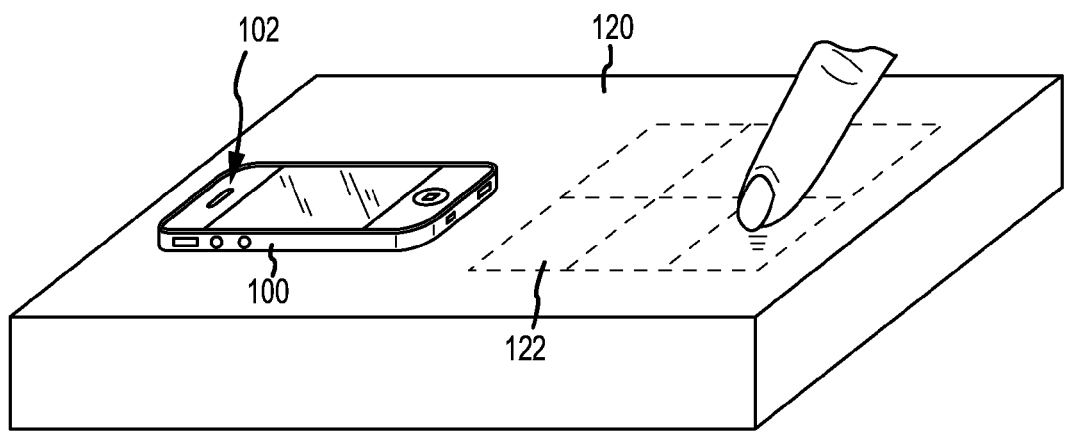
FIG. 1 shows a conceptual drawing of a frequency device on a surface.

FIG. 1 shows a conceptual drawing of a frequency device on a surface.

A frequency device 100 can be disposed on a resonant surface 120, or can be coupled to one or more objects collectively having at least one such surface 120.

In one embodiment, the frequency device 100 can include a speaker 102, disposed to emit one or more acoustic signals. For a first example, the one or more acoustic signals can include an acoustic impulse, such as a click or a pulse, or otherwise disposed to elicit a sonic impulse response from a sonic medium. For a second example, the acoustic signals can include one or more selected frequencies, or combinations or conjunctions thereof, such as one or more pure frequencies, or one or more dual-tone multi-frequency (DTMF) sounds. For a third example, the acoustic signals can include one or more swept-sinusoid signals, or combinations or conjunctions thereof, or other known time-varying signals, such as ramped triangular waves, square waves, or otherwise.

In one embodiment, the frequency device 100 can include a vibration sensor 104 (shown in FIG. 6), disposed to receive one or more acoustic signals, such as signals mediated by the surface 120. For example, the vibration sensor 104 can include an accelerometer, an inertial response sensor, or other device disposed to receive vibrations from the surface 120.

In one embodiment, the frequency device 100 can include a sonic sensor 106 (shown in FIG. 6), disposed to receive one or more acoustic signals, such as those mediated by an ambient atmosphere or other sonic medium. For example, the sonic sensor 106 can include a microphone or other device disposed to receive acoustic signals emitted by the surface 120.

In one embodiment, the surface 120 can be disposed to have a shape and size, and include one or more materials from which it is manufactured. For a first example, the surface 120 can be made of metal, plastic, wood, or another substance. For a second example, the surface 120 can be laminated or covered with a secondary substance, such as a metal or wooden surface laminated with a plastic covering. The shape and size, and one or more materials, can have the effect that the surface 120 has an acoustic impulse response and one or more resonant frequencies. As described herein, the resonant frequencies of the surface 120 can have the property that an acoustic signal (or portion thereof) having one of those resonant frequencies would be amplified when applied to the surface 120, and that the amplification would be (at least locally) maximized.

This can have the effect that when the frequency device 100 applies, using the speaker 102, an acoustic signal including one or more of the resonant frequencies to the surface 120, the surface 120 would amplify the portion of that acoustic signal including the resonant frequencies, and would provide to the frequency device 100 and returned acoustic signal in which the resonant frequencies would be amplified. This can have the effect that the vibration sensor 104 and the sonic sensor 106 of the frequency device 100 would detect the returned acoustic signal with the portion of the resonant frequencies having been amplified. This can have the effect that the frequency device 100 can detect the resonant frequencies in response to the surface 120. For example, the frequency device 100 can determine those frequencies at which the surface 120 returns a signal that is maximally amplified.

In one embodiment, the frequency device 100 can include a processor 108 (shown in FIG. 6), associated with program and data memory 110 (shown in FIG. 6), disposed to interpret instructions in the program and data memory 110, and disposed to execute those instructions to provide one or more acoustic signals to the surface 120. For example, the frequency device 100 can be disposed to provide acoustic signals to the surface 120 including one or more impulse vibrations, one or more frequencies, or one or more swept-sinusoids emitted by the frequency device 100. In such cases, the frequency device 100 can be disposed to provide impulse vibrations as described in any known text describing generation and transmission of impulse signals, emitted as sound. In such cases, the frequency device 100 can be disposed to provide one or more frequencies as described in any known text describing generation and transmission of known frequencies, whether pure or mixed, emitted as sound. In such cases, the frequency device 100 can be disposed to provide one or more swept-sinusoids as described in any known text describing generation and transmission of signals having sine waves of known varying frequencies, emitted as sound.

In one embodiment, the surface 120 can include a relatively flat, relatively solid object, such as a desk or a tabletop. For example, the surface 120 can include one or more regions 122 on which a user (not shown) can poke, scratch, slide, tap, or otherwise cause a vibration or other sonic impulse. This can have the effect that the surface 120, when the user taps on one such region 122, emits a sonic impulse that can be received and interpreted by the frequency device 100.

In one embodiment, the regions 122 into which the surface 120 is divided can indicate specific signals or symbols, such as could be used as a substitute for typewriter keys. In one embodiment, lines or boxes, or typography indicative of those signals or symbols, or other indicators for those signals or symbols, can be projected by the frequency device 100, or another device, onto the surface 120. This can have the effect that the regions 122 of the surface 120 can be so divided that the frequency device 100 can detect one of a multiplicity of such signals or symbols. This can have the effect that the surface 120 can be used, in combination with the frequency device 100, to determine in what region 122 on the surface 120 the sonic impulse occurred. For a first example, the user can tap in one of the corners of the surface 120, and the frequency device 100 can determine which corner. For a second example, the user can tap in one of a multiplicity of small regions 122 of the surface 120, and the frequency device 100 can determine which of those small regions 122. In such cases, the multiplicity of small regions 122 could emulate a keyboard or other form of touchable control element.

In one embodiment, the frequency device 100 may pre-calibrate a set of locations where the user would swipe or tap on the surface 120. (In one embodiment, the frequency device 100 may detect when the user swipes on the surface 120, in addition to or in alternative to tapping on the surface 120.) In one embodiment, the frequency device 100 may pre-calibrate locations by asking the user to swipe or tap at each location in turn. For a first example, the user could swipe or tap at each location in an order requested by the frequency device 100, or by swiping or tapping at locations using a code to indicate which location, such as Morse code or another known code for representing symbols, or by swiping or tapping at locations using another fixed signal already known to the frequency device 100. This would have the effect that the frequency device 100 could match the indicated symbol with the acoustic signal associated with that location, thus identifying that symbol with that location. For a second example, the user could swipe or tap at each location with a user-defined identifiable set of touches for each such symbol, with the effect that the frequency device 100 could match the indicated symbol with the user-defined identifiable set of touches and its associated acoustic signal.

In one embodiment, the user may place a printed keyboard, such as made of paper or plastic, under the frequency device 100. The printed keyboard may indicate a location of where to tap or slide to indicate particular keys or controls. For a first example, a plastic keyboard may include a material with a relatively high resolution of location, by its own impulse response or resonant frequency. For a second example, the locations of keys or controls may be pre-determined by calibration of the frequency device 100 with respect to the surface 120, such as described above, with the effect that the frequency device 100 would have relatively good resolution of where the user swipes or taps, and without substantial overlap of acoustic signals. For a third example, the printed keyboard may include a set of ridges or other surface features, such that swiping a finger (or other implement, such as a stylus) on or near those surface features would be detectable by the frequency device 100.

In one embodiment, in cases in which the regions 122 of the surface 120 can be divided into a multiplicity of letters or symbols such as a virtual keyboard, the virtual keyboard can be combined with a display and dynamically adjusted to alter the letters or symbols associated with each key in response to one or more time-varying circumstances. For a first example, the virtual keyboard can be adjusted to use a "SHIFT" key to change the presentation of letters or symbols to indicate upper-case characters instead of lower-case characters. For a second example, the virtual keyboard can be adjusted to show diacritical marks or a secondary set of letters or symbols in response to a function key, such as with a scientific calculator.

While the frequency device 100 and the surface 120, and associated elements, have been described with respect to one or more particular embodiments, alternative embodiments are possible that remain within the scope and spirit of the invention, would be clear to those of ordinary skill in the art after reading this application, and would not require either further invention or undue experiment.

First Method of Operation

Figure 2:
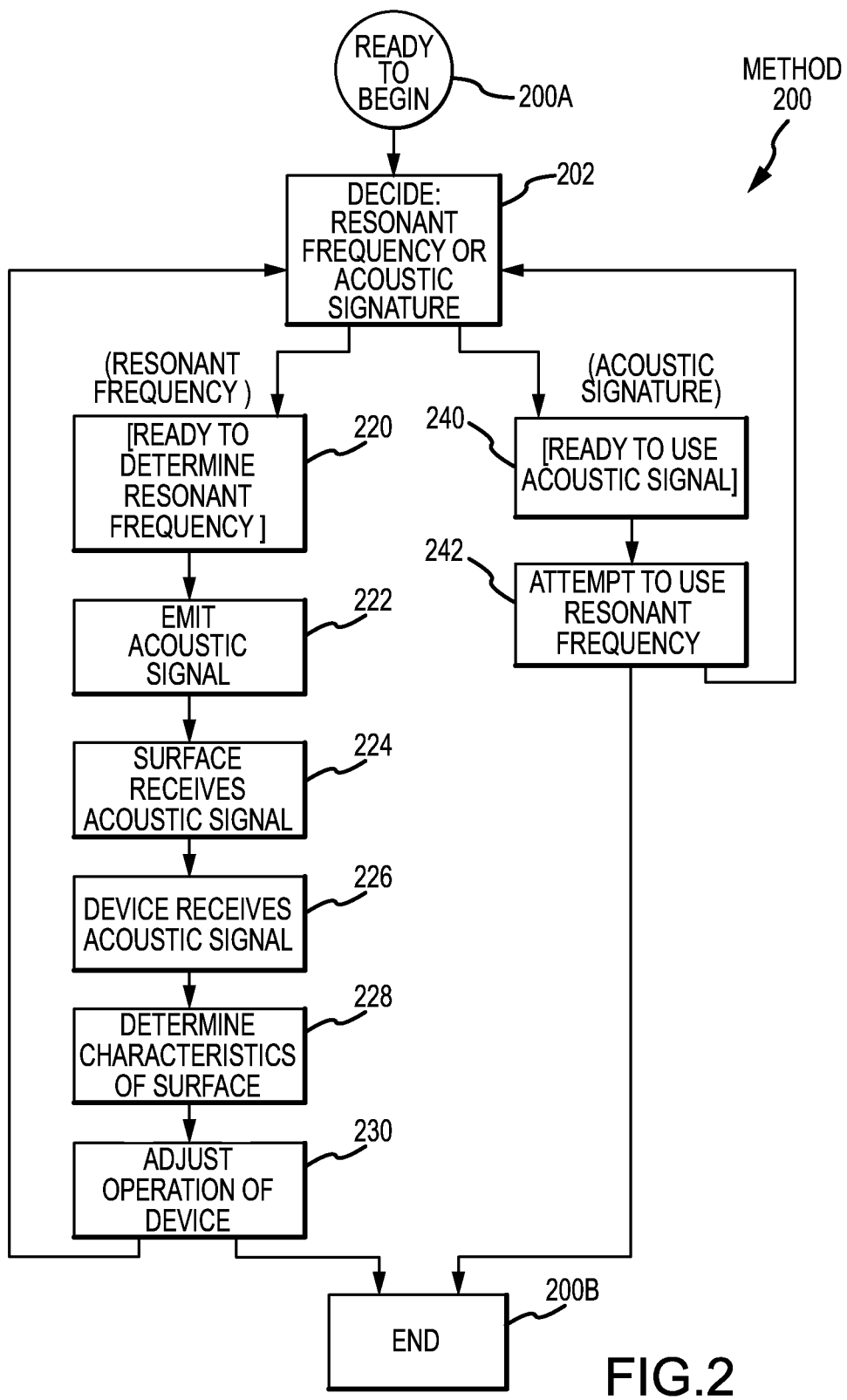
FIG. 2 shows a conceptual drawing of a first example method of operation.

FIG. 2 shows a conceptual drawing of a first method of operation.

A first method 200 includes a set of flow points and method steps. In one embodiment, the method 200 can enable the frequency device 100 to determine one or more resonant frequencies of the surface 120, and in response to those one or more resonant frequencies, determine information about the surface (such as a shape, size, and composition material of the surface 120). In one embodiment, the method 200 can enable the frequency device 100 to use the resonant frequencies of the surface 120, such as to use the surface 120 as an alarm or noise generator, to use the surface 120 as an amplifier for music or other sound, to find studs, weak points, or other irregularities within the surface 120, and otherwise.

Although these flow points and method steps are sometimes described as performed in a particular order, in the context of the invention, there is no particular requirement for any such limitation. For example, the flow points and method steps could be performed in a different order, concurrently, in parallel, or otherwise. Similarly, although these flow points and method steps are shown performed by a general purpose processor in a force sensitive device, in the context of the invention, there is no particular requirement for any such limitation. For example, one or more such method steps could be performed by special purpose processor, by another circuit, or be offloaded to other processors or other circuits in other devices, such as by offloading those functions to nearby devices using wireless technology or by offloading those functions to cloud computing functions.

Although these flow points and method steps are sometimes described as performed by the method 200, they are substantially performed by elements with respect to one or more devices or systems as described herein. For example, one or more such method steps could be performed by the frequency device 100, by the surface 120 (or by devices coupled thereto), by a portion thereof, by a combination or conjunction thereof, or by other devices or systems as described herein. Moreover, one or more such method steps could be performed by other devices or systems not explicitly described herein, but which would be clear to those of ordinary skill in the art after reading this application, and which would not require either further invention or undue experimentation.

At a flow point 200a, the method 200 is ready to begin.

At a step 202, the frequency device 100 can decide whether it will attempt to determine resonant frequencies of the surface 120, or whether it will attempt to receive an acoustic signal from the surface 120. If the frequency device 100 decides it will attempt to determine resonant frequencies of the surface 120, the method 200 proceeds with the flow point 220. If the frequency device 100 decides it will attempt to receive an acoustic signal from the surface 120, the method 200 proceeds with the flow point 240. In alternative embodiments, the frequency device 100 can proceed with both flow points 220 and 240 in parallel.

At the flow point 220, the frequency device 100 is ready to determine resonant frequencies of the surface 120. In one embodiment, the frequency device 100 can attempt to determine information about one or more resonant frequencies of the surface 120 by emitting an acoustic signal and receiving a response from the surface 120.

At a step 222, the frequency device 100 can emit one or more acoustic signals, such as at the surface 120. This can have the effect that the acoustic signal is transmitted to the surface 120. For example, the acoustic signal can include an impulse vibration, one or more selected frequencies, a time-varying signal such as a swept-sinusoid, or otherwise.

For a first example, if the frequency device 100 is positioned near or on top of the surface 120, and the frequency device 100 includes a speaker 102, the frequency device 100 can emit a sound that propagates through at least a portion of the surface 120. For a second example, if the on top of the surface 120, and the frequency device 100 includes a haptic element such as a vibrating element, the frequency device 100 can emit a vibration impulse that propagates through at least a portion of the surface 120.

In one embodiment, the frequency device 100 can include a mobile media player, such as an iPod™, iPhone™, or iPad™, or another type of related device, interpreting or executing instructions from an application program.

In one embodiment, the acoustic signal includes a swept-sinusoid. This can have the effect that substantially each frequency within the range of the swept-sinusoid that might be a resonant frequency is presented to the surface 120 as part of an acoustic signal, with the effect that the surface 120 can respond by relatively amplifying the resonant frequency components of that acoustic signal, and relatively damping non-resonant frequency components of that acoustic signal.

In one embodiment, the surface 120 can include a flat surface such as a keyboard (or a flat object painted to look like a keyboard), a table, or some other object. While this application primarily describes surfaces 120 that are substantially flat and have substantially smooth layers, in the context of the invention, there is no particular requirement for any such limitation. For example, one or more such surfaces 120 could be curved, could have ribbed or ridged lines or other texture, or otherwise. As described herein, for example, one or more such surfaces 120 could also include cracks, leaks, studs, or other irregularities, with concomitant effect on the resonant frequencies of such surfaces 120.

At a step 224, the surface 120 can receive the acoustic signal. This can have the effect that the surface 120 relatively amplifies the one or more frequencies included in the signal that are resonant frequencies of the surface 120, and relatively dampens any frequencies that are not resonant frequencies in the signal. For example, if the surface 120 has a resonant frequency of about 1 KHz, the surface 120 provides a response (whether to an impulse vibration, a set of selected frequencies, a swept-sinusoid, or otherwise) in which the resonant frequency is relatively pronounced.

At a step 226, the frequency device 100 receives, from the surface 120, one or more responses to the acoustic signal. In one embodiment, the frequency device 100 can analyze the response and determine resonant frequencies of the surface 120. For a first example, the frequency device 100 can determine each of the resonant frequencies of the surface 120, or can determine a resonant frequency of the surface 120 with the highest relative amplification. For a second example, the frequency device 100 can determine an impulse response of the surface 120, either in response to the resonant frequency (or frequencies) of the surface 120, or in response to a comparison of the emitted acoustic signal with the received acoustic signal.

At a step 228, the frequency device 100, in response to a result from the previous step, can determine one or more characteristics of the surface 120. For example, the frequency device 100 can determine one of: a shape, size, or construction material of the surface 120, in response to information about the other two of them.

At a step 230, the frequency device 100 can adjust its operation in response to information about the object. This can have the effect of improving performance of the device in one or more characteristics. For example, should the frequency device 100 determine a resonant frequency of the surface 120, the frequency device 100 can adjust its operation so that it uses that resonant frequency as a center frequency for sonic output (such as a center frequency for playing music). As described herein, in one embodiment, the frequency device 100 can make other and further adjustments to its operation, with the effect of operating with the surface 120 to greater value.

In one embodiment, the method 200 can continue with step 202, at which it re-decides whether it will attempt to determine resonant frequencies of the surface 120, or whether it will attempt to receive an acoustic signal from the surface 120. In alternative embodiments, the method 200 can continue with the flow point 200b, at which the method 200 is complete, and can be repeated.

At the flow point 240, the frequency device 100 is ready to use one or more of the resonant frequencies of the surface 120.

At a step 242, the frequency device 100 attempts to use one or more of the resonant frequencies of the surface 120. As part of this step, the frequency device 100 can attempt one or more of several different uses of the resonant frequencies, as described below:

For a first example, the frequency device 100 can emit an acoustic signal having one or more of the resonant frequencies of the surface 120 as a significant component. In such cases, the surface 120 would respond by amplifying those resonant frequencies. This could have the effect of generating and emitting a relatively loud noise, such as could be used as an alarm.

For a second example, the frequency device 100 can emit an acoustic signal with one of the resonant frequencies as a center frequency for a sound to be amplified, such as music or speech. This could have the effect of generating and emitting an amplified version of the sound. In such cases, the music or speech would be reproduced at a louder volume than the device itself might be able to attain, such as from a loudspeaker.

For a third example, the frequency device 100 can emit an acoustic signal with one of the resonant frequencies as a finder for studs or other irregularities in the surface 120 (such as cracks or leaks), that is, a finder for elements in the surface 120 that differ in density or substance from a remainder of the surface 120. Such elements could have the effect that the resonant frequencies of the surface 120 would be different at distinct locations near or on the surface 120. In one embodiment, the frequency device 100 can be moved about until one or more such studs are detected or located.

For example, the detected resonant frequencies of the surface 120 would be different in a "normal" region 122 of the surface 120, from the detected resonant frequencies would be in a region 122 near or on a stud (or other irregularity, such as a crack or a leak). This could be due to a stud or other irregularity having a different density underneath a top layer of the surface 120. In one embodiment, the frequency device 100 can emit an acoustic signal including one or more of the resonant frequencies of the surface 120 in the "normal" regions 122 of the surface 120. Should the frequency device 100 be moved near or on a stud or other irregularity, it could find that those frequencies would not be resonant frequencies near or on such a stud or other irregularity. This could have the effect that the frequency device 100 would be able to detect and locate studs or other irregularities underneath a top layer of the surface 120.

In one embodiment, the method 200 can continue with the step 202, at which it re-decides whether it will attempt to determine resonant frequencies of the surface 120, or whether it will attempt to receive an acoustic signal from the surface 120. In alternative embodiments, the method 200 can continue with the flow point 200b, at which the method 200 is complete, and can be repeated.

At a flow point 200b, the method 200 is complete. In one embodiment, the method 200 is repeated so long as the frequency device 100 is powered on, or if operating under control of an application program, the method 200 is repeated so long as the application program directs it to.

Second Method of Operation

Figure 3:
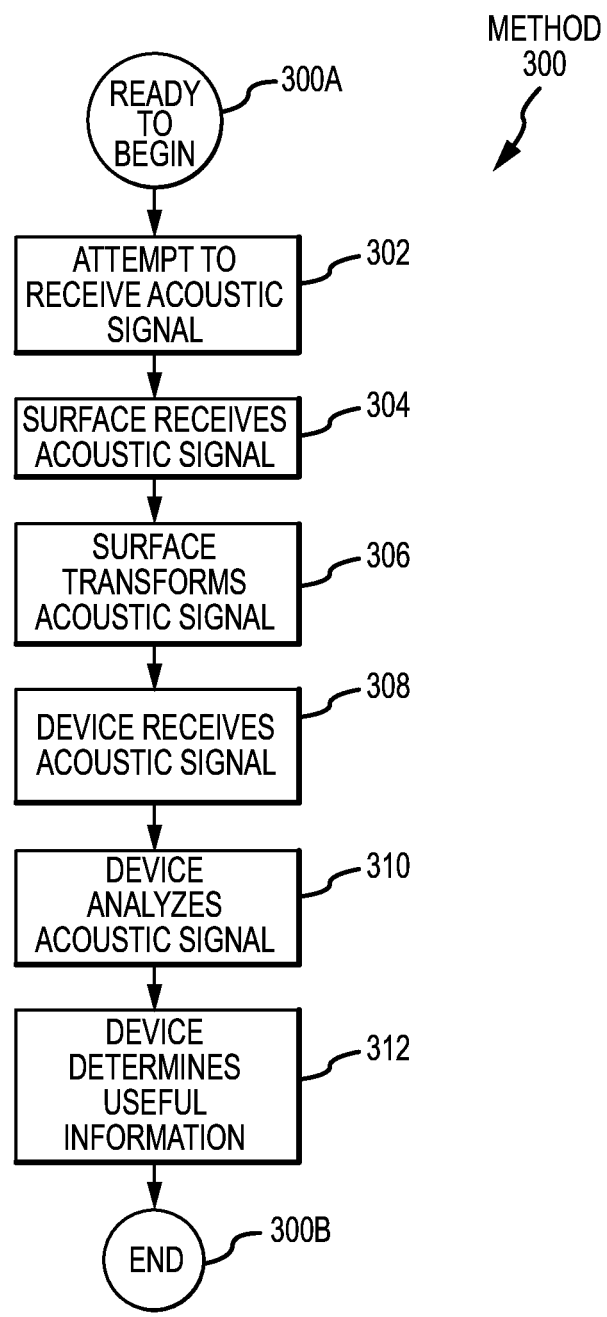
FIG. 3 shows a conceptual drawing of a second example method of operation.

FIG. 3 shows a conceptual drawing of a second method of operation. In one embodiment, the method 300 can enable the frequency device 100 to receive vibration signals from the surface 120, in response to one or more resonant frequencies of that surface 120, and determine characteristics about those vibration signals (such as a duration, location, pressure, or otherwise).

A second method 300 includes a set of flow points and method steps. In one embodiment, the method 300 can enable the frequency device 100 to sense acoustic vibrations from an object, such as received from a finger or stylus applied to the object, or from a device applied to the object. In one embodiment, the frequency device 100 can adjust its operation in response to the vibrations, such as constructing input data. For example, the frequency device 100 can receive vibrations from one or more locations on a tabletop, and can, in response to a measure of how much the tabletop amplifies or dampens vibrations from those locations, emulate a keyboard, keypad, mouse or trackpad, game controller, musical instrument control, or other input for a computing device.

Although these flow points and method steps are sometimes described as performed in a particular order, in the context of the invention, there is no particular requirement for any such limitation. For example, the flow points and method steps could be performed in a different order, concurrently, in parallel, or otherwise. Similarly, although these flow points and method steps are shown performed by a general purpose processor in a force sensitive device, in the context of the invention, there is no particular requirement for any such limitation. For example, one or more such method steps could be performed by special purpose processor, by another circuit, or be offloaded to other processors or other circuits in other devices, such as by offloading those functions to nearby devices using wireless technology or by offloading those functions to cloud computing functions.

Although these flow points and method steps are sometimes described as performed by the method 200, they are substantially performed by elements with respect to one or more devices or systems as described herein. For example, one or more such method steps could be performed by the frequency device 100, by the surface 120 (or by devices coupled thereto), by a portion thereof, by a combination or conjunction thereof, or by other devices or systems as described herein. Moreover, one or more such method steps could be performed by other devices or systems not explicitly described herein, but which would be clear to those of ordinary skill in the art after reading this application, and which would not require either further invention or undue experiment.

At a flow point 300a, the method 300 is ready to begin.

At a step 302, the frequency device 100 can attempt to receive an acoustic signal from the surface 120.

At a step 304, the surface 120 receives the acoustic signal. For a first example, the acoustic signal can include an impulse vibration imposed on the surface 120, such as a finger tap on a location somewhere on the surface 120. For a second example, the acoustic signal can include a more complex acoustic signal imposed on the surface 120, such as by a device (such as a pen, stylus, or vibrating element), and can include one or more selected frequencies.

At a step 306, the surface 120 transforms the acoustic signal in accordance with the impulse response of the surface 120. For example, the impulse response of the surface 120 can have the property of providing one or more resonant frequencies. As described herein, this can have the effect that the surface 120 relatively amplifies the one or more component frequencies included in the acoustic signal that are resonant frequencies, and relatively dampens any component frequencies included in the acoustic signal that are not resonant frequencies. The one or more resonant frequencies of the surface 120 can have the properties that the frequency device 100 can determine the impulse response of the surface 120 in response thereto.

At a step 308, the frequency device 100 receives, from the surface 120, one or more responses to the acoustic signal. For a first example, the surface 120 can send a main response to the acoustic signal, which the frequency device 100 detects. For a second example, the surface 120 can send more than one response to the acoustic signal by means of distinct acoustic paths, which the frequency device 100 can detect. In such cases, sometimes referred to herein as "multipath" cases, the more than one response to the acoustic signal can occur because the acoustic signal is reflected from one or more edges of the surface, or is refracted by one or more portions of the surface 120.

At a step 310, the frequency device 100 can analyze the response and determine resonant frequencies of the surface 120. For a first example, the frequency device 100 can determine each of the resonant frequencies of the surface 120, or can determine a resonant frequency of the surface

120 with the highest relative amplification. For a second example, the frequency device 100 can determine an impulse response of the surface 120, either in response to the resonant frequency (or frequencies) of the surface 120, or in response to a comparison of the emitted acoustic signal with the received acoustic signal.

In one embodiment, the frequency device 100 receives the acoustic signal, and filters it to reduce noise. In one embodiment, having filtered the acoustic signal, the frequency device 100 analyzes a waveform of the received and filtered acoustic signal, and determines an impulse response of the surface 120 in response thereto. In one embodiment, the frequency device 100, having determined an impulse response of the surface 120, determines the one or more resonant frequencies of the surface 120 in response thereto.

For a first example, if more than one resonant frequency exists, the frequency device 100 attempts to determine all of them. Should there be multiple resonant frequencies, the resonant frequencies above the base may be a multiple of the fundamental resonant frequency. In one embodiment, if a microphone or other vibration element of the frequency device 100 has only some of those resonant frequencies within its range, the frequency device 100 records only those resonant frequencies within its range.

For a second example, should the frequency device 100 send a time-varying swept-sinusoid acoustic signal to the surface 120, the surface 120 should provide a response that relatively amplifies the one or more component frequencies included in the acoustic signal that are resonant frequencies, and relatively dampens any component frequencies included in the acoustic signal that are not resonant frequencies. In such cases, the frequency device 100 can determine the one or more resonant frequencies of the surface 120 in response to which component frequencies are relatively amplified and which component frequencies are relatively damped. This can have the effect that, instead of attempting to determine an impulse response for the surface 120, the frequency device 100 can record which component frequencies are relatively most amplified by the surface 120.

At a step 312, the frequency device 100 attempts to determine, in response to the acoustic signal, useful information about the acoustic signal. In one embodiment, the frequency device 100 attempt to determine one or more of the following about the acoustic signal: duration, location, volume, and materials used to induce the acoustic signal.

In one embodiment, the frequency device 100 could maintain a pre-defined database of impulse responses and/or step responses of distinct materials. This could have the effect that the frequency device 100 could determine the nature of the surface 120 (such as its material), or other useful information about the surface 120 (such as its size, shape, and other features) in response to a comparison of the acoustic signal with one or more of those impulse responses and/or step responses. For a first example, the frequency device 100 could have its own vibrational information and location information of its own speaker 102, vibration sensor 104, and sonic sensor 106, as relatively located within the its housing, which the frequency device 100 could take into consideration when comparing the acoustic signal with those impulse responses and/or step responses. For a second example, the user could provide the frequency device 100 with information (such as an estimate) about the size or shape of the surface 120, such as by using a keyboard or other touch input directly on the frequency device 100. This could have the effect that the frequency device 100 could take this information into account when analyzing acoustic signals from the surface 120. For a third example, the user could provide the frequency device 100 with one or more examples of relatively "normal" strength taps on the surface 120, in contrast with relatively "soft" taps or relatively "hard" taps. This could have the effect that the frequency device 100 could compare relatively "soft" taps or relatively "hard" taps with relatively "normal" strength taps, such as using the vibration sensor 104 and sonic sensor 106, and could identify a relative wider variety of acoustic signals. For a fourth example, the frequency device 100 could include more than one vibration sensor 104, more than one sonic sensor 106, or maintain its vibration sensor 104 and its sonic sensor 106 at a relative distance. This could have the effect that the frequency device 100 could use the separation between multiple sensors to triangulate a location of original of the acoustic signal on the surface 120.

For a first example, the frequency device 100 can attempt to determine a location from which the acoustic signal originated, such as in response to an amount of relative amplification of one or more resonant frequencies, or an amount of relative damping of one or more non-resonant frequencies. In such cases, the frequency device 100 can attempt to determine a distance the acoustic signal traveled, such as in response to an amount of relative amplification or damping, or in response to a number of multipaths, in response to a time delay as compared with a calibration location, or otherwise. In such cases, the frequency device 100 can attempt to determine a direction the acoustic signal came from, such as in response to a phase delay of the acoustic signal with respect to more than one receiver (such as a stereo receiver), or otherwise. In alternative embodiments, the frequency device 100 can attempt to determine a location from which the acoustic signal originated in response to calibration, by a user tapping at each distinct location to be identified.

For a second example, the frequency device 100 can attempt to determine a duration of the acoustic signal, such as in response to a relative volume of an envelope of the acoustic signal. In such cases, the frequency device 100 could determine that the duration of the acoustic signal includes that time duration when the acoustic signal exceeds a signal to noise threshold, or otherwise.

For a third example, the frequency device 100 can attempt to determine a volume of the acoustic signal, such as in response to a relative volume of an envelope of the acoustic signal. In such cases, the frequency device 100 could determine that the volume of the acoustic signal is responsive to a average peak value of the acoustic signal, or otherwise.

In one embodiment, should the frequency device 100 determine a particular region 122 from which the acoustic signal originated in enough detail, the frequency device 100 can determine a typewriter key, letter, or other symbol as an input from a user. In one embodiment, the frequency device 100 can accept that input for itself, or can direct that input to another device. In alternative embodiments, the frequency device 100 could determine a location to be used as input for a game controller or other device, such as a motion-oriented game.

For example, the frequency device 100 could determine inputs for one or more of the following: (A) The frequency device 100 could determine inputs for a music player, such as one tap to start a song, two taps to pause a song, and otherwise. (B) The frequency device 100 could determine inputs for a game or other application, such as drumming with one or more fingers to indicate inputs to single-player games or multiplayer games. (C) The frequency device 100 could determine inputs for an authentication technique, password, unlock code, or other security measure, such as requiring a user to present a specific drumming or tapping pattern. In one embodiment, the pattern could be specific in location, specific in time, or both, or otherwise.

In one embodiment, the pattern could authenticate a specific user or otherwise indicate that the frequency device 100 should respond to particular commands.

The method 300 continues with the flow point 300*b*.

At a flow point 300*b*, the method 300 is complete. In one embodiment, the method 300 is repeated so long as the device is powered on.

Cooperating Frequency Devices

Figure 4:
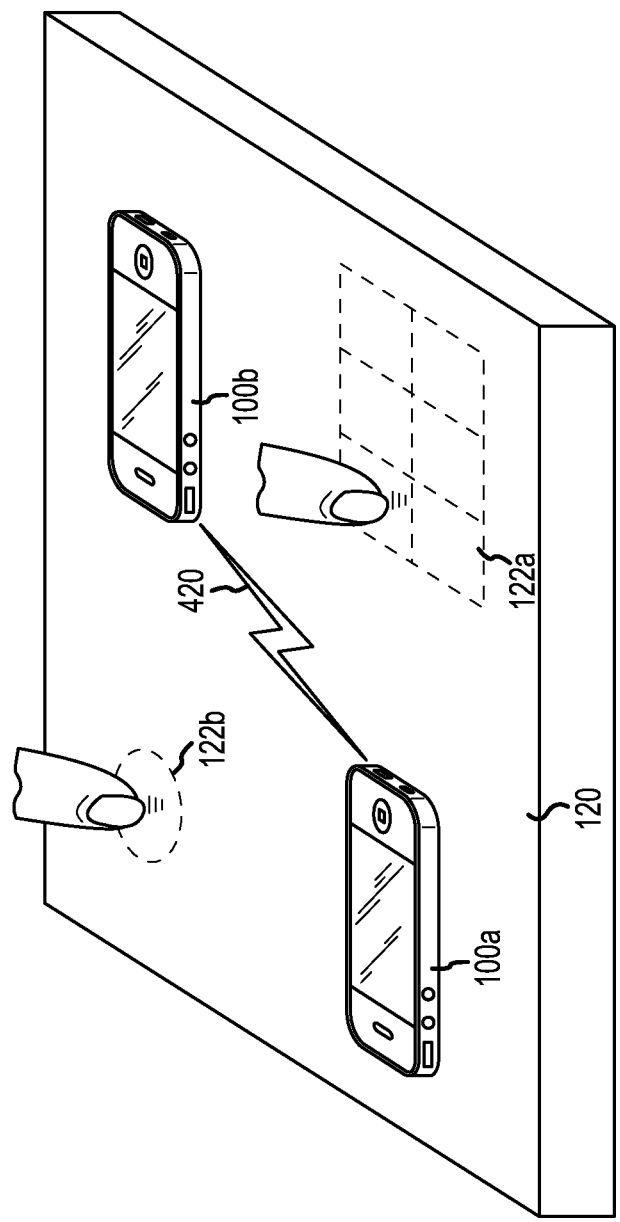
FIG. 4 shows a conceptual drawing of a two frequency devices cooperating on a surface.

FIG. 4 shows a conceptual drawing of a two frequency devices cooperating on a surface.

A first frequency device 100*a* and a second frequency device 100*b* can be disposed on a surface 120, or can be coupled to one or more objects collectively having at least one such surface 120. In one embodiment, each frequency device 100*a* and 100*b* can include a speaker 102, a vibration sensor 104 (shown in FIG. 6), a sonic sensor 106 (shown in FIG. 6), a processor 108 (shown in FIG. 6), associated with program and data memory 110 (shown in FIG. 6), and otherwise, similar to the frequency device 100 described with respect to the FIG. 1.

In one embodiment, the surface 120 can be disposed to have a shape and size, and include one or more materials from which it is manufactured, similar to the surface 120 described with respect to the FIG. 1. The surface 120 can include one or more regions 122*a* and 122*b*, similar to the regions 122 described with respect to the FIG. 1.

In one embodiment, the first frequency device 100*a* and the second frequency device 100*b* can communicate using an electronic communication link 420, such as a Bluetooth™ communication link, a cellular telephone communication link, a packet switched communication link, or otherwise.

In one embodiment, collectively, the first frequency device 100*a* and the second frequency device 100*b* can include at least one acoustic emitter and at least one acoustic sensor. This can have the effect that the first frequency device 100*a* and the second frequency device 100*b* can send acoustic signals from a first location (such as where the first frequency device 100*a* is located) and receive acoustic signals at a second location (such as where the second frequency device 100*a* is located). In one embodiment, collectively, the first frequency device 100*a* and the second frequency device 100*b* can include at least one electronic emitter and at least one electronic sensor. This can have the effect that the first frequency device 100*a* and the second frequency device 100*b* can send electromagnetic signals between the first frequency device 100*a* and the second frequency device 100*b*.

In one embodiment, the first frequency device 100*a* and the second frequency device 100*b* can emit acoustic signals from one of the two frequency devices 100*a* and 100*b*, mediate those acoustic signals using the surface 120, and can receive those acoustic signals at the other of the two frequency devices 100*a* and 100*b*. The first frequency device 100*a* and the second frequency device 100*b* can also send information electronically, such as using the electronic communication link 420, describing the nature of the acoustic signals that were sent, and comparing them with the nature of the acoustic signals that were received.

In one embodiment, one of the two frequency devices 100*a* and 100*b* can be disposed to emit an acoustic signal including a selected frequency for which a frequency response from the surface 120 is known to at least one of the two frequency devices 100*a* and 100*b*. The other of the two frequency devices 100*a* and 100*b* can be disposed to receive that selected frequency, and compare the sent acoustic signal with the received acoustic signal. Having compared the sent acoustic signal with the received acoustic signal, collectively, the two frequency devices 100*a* and 100*b* can determine an impulse response or a resonant frequency of the tabletop.

Third Method of Operation

Figure 5:
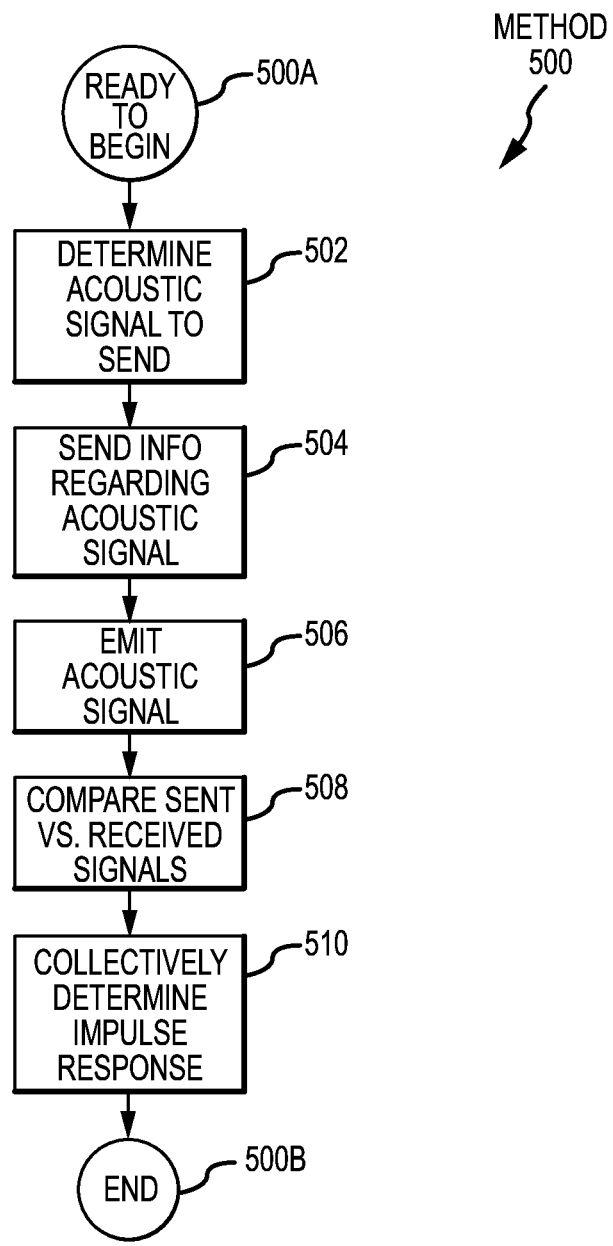
FIG. 5 shows a conceptual drawing of a third example method of operation.

FIG. 5 shows a conceptual drawing of a third method of operation.

A third method 500 includes a set of flow points and method steps.

Although these flow points and method steps are sometimes described as performed in a particular order, in the context of the invention, there is no particular requirement for any such limitation. For example, the flow points and method steps could be performed in a different order, concurrently, in parallel, or otherwise. Similarly, although these flow points and method steps are shown performed by a general purpose processor in a force sensitive device, in the context of the invention, there is no particular requirement for any such limitation. For example, one or more such method steps could be performed by special purpose processor, by another circuit, or be offloaded to other processors or other circuits in other devices, such as by offloading those functions to nearby devices using wireless technology or by offloading those functions to cloud computing functions.

Although these flow points and method steps are sometimes described as performed by the method 200, they are substantially performed by elements with respect to one or more devices or systems as described herein. For example, one or more such method steps could be performed, either individually or collectively, by the frequency devices 100*a* and 100*b*, by the surface 120, by a portion thereof, by a combination or conjunction thereof, or by other devices or systems as described herein. Moreover, one or more such method steps could be performed by other devices or systems not explicitly described herein, but which would be clear to those of ordinary skill in the art after reading this application, and which would not require either further invention or undue experiment.

At a flow point 500*a*, the method 500 is ready to begin. The method 500 can coordinate devices, such as having at least one acoustic emitter and at least one acoustic sensor, and coupled using one or more electronic communication links 420. For example, the devices could include the frequency device 100*a* and 100*b*, and could communicate acoustic signals mediated by the surface 120.

At a step 502, the first frequency device 100*a* determines an acoustic signal to send to the second frequency device 100*b*. For a first example, the first frequency device 100*a* can select an acoustic signal including one or more known frequency components, such as a time-varying swept-sinusoid acoustic signal. For a second example, the first frequency device 100*a* can select an acoustic signal including components for which the impulse response or the resonant frequencies of the surface 120 are believed to be known.

At a step 504, the first frequency device 100*a* sends information with respect to the acoustic signal (as determined in the previous step) to the second frequency device 100*b*, such as using the electronic link 420. In alternative embodiments, if the nature of the surface 120 permits, the first frequency device 100*a* can send information with respect to the acoustic signal to the second frequency device 100*b* using an acoustic signal. For example, the first frequency device 100*a* can send a distinct acoustic signal with that information to the second frequency device 100b, or can encode that information in the same acoustic signal. As part of this step, the second frequency device 100b receives the information about the acoustic signal.

At a step 506, the first frequency device 100a emits an acoustic signal to the surface 120, the surface 120 propagates the emitted acoustic signal to the second frequency device 100b, and the second frequency device 100b receives the propagated acoustic signal. This can have the effect that the emitted acoustic signal is mediated by the surface 120 during transmission from the first frequency device 100a to the second frequency device 100b.

At a step 508, in one embodiment, the second frequency device 100b can compare the emitted acoustic signal with the received acoustic signal. In alternative embodiments, the second frequency device 100b sends information with respect to the received acoustic signal to the first frequency device 100a, which can compare the emitted acoustic signal with the received acoustic signal. Either way, the first frequency device 100a and the second frequency device 100b can collectively compare the emitted acoustic signal with the received acoustic signal.

At a step 510, the first frequency device 100a and the second frequency device 100b can collectively determine an impulse response of the surface 120, or a set of one or more resonant frequencies of the surface 120. The first frequency device 100a and the second frequency device 100b can exchange information so that both have sufficient information to determine that impulse response or those resonant frequencies.

Having determined that impulse response or those resonant frequencies, the first frequency device 100a and the second frequency device 100b can proceed similarly to the methods 200 and 300 described with respect to the FIG. 2 and the FIG. 3.

The method 500 proceeds with the flow point 500b.

At a flow point 500b, the method 500 is complete. In one embodiment, the method 500 is repeated so long as the devices are powered on.

Frequency Device Components

Figure 6:
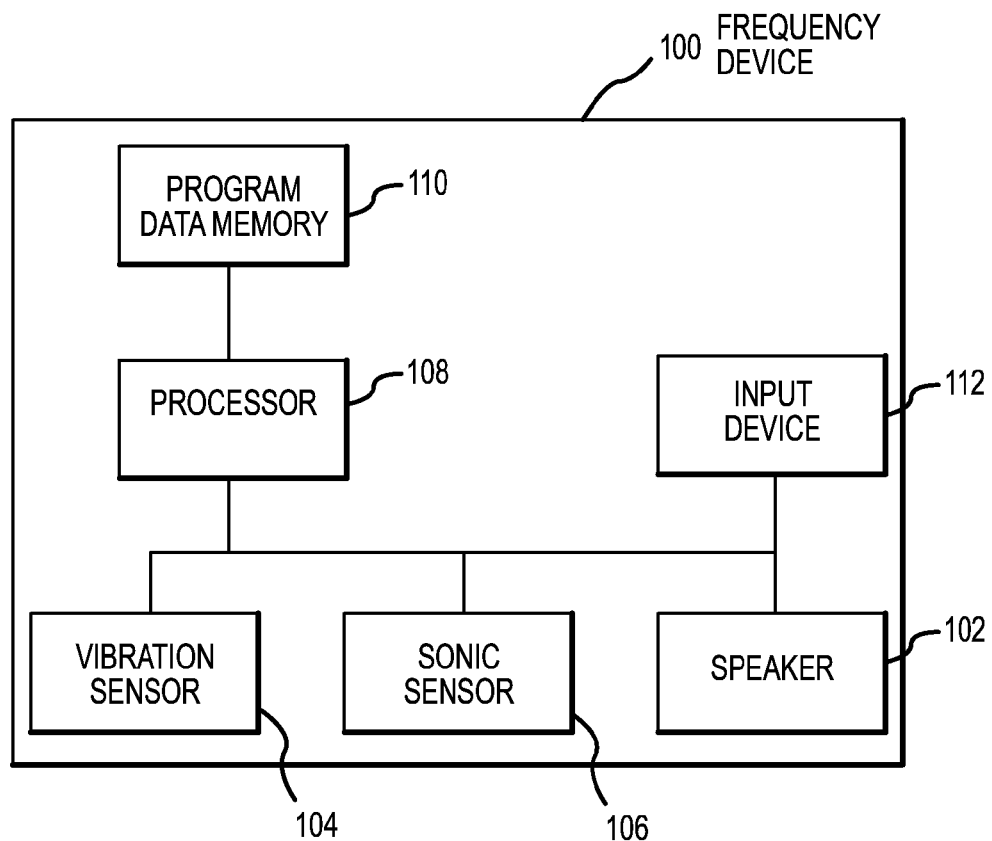
FIG. 6 shows a conceptual drawing of a frequency device.

FIG. 6 shows a conceptual drawing of a frequency device.

The frequency device 100 can include a processor 108, and program and data memory 110 including instructions interpretable by the processor 108 to perform methods as described herein, either alone or in combination or conjunction with a one or more additional frequency devices 100.

The frequency device 100 can include a speaker 102, a vibration sensor 104, and a sonic sensor 106, as described above. The speaker 102 can be disposed to emit acoustic signals, as described above. The vibration sensor 104 can include an accelerometer or other inertial response sensor, and can be disposed to detect vibrations in or on the surface 120, as described above. The sonic sensor 106 can include a microphone or other sonic-sensitive element, and can be disposed to detect acoustic signals in or on the surface 120, as described above.

The frequency device 100 can include an input device 112, such as a keyboard, disposed to allow the user to provide information to the frequency device 100, as described above. For example, the input device 112 can include a touch-sensitive virtual keyboard presented on a display, such as provided by an iPhone™ or similar device.

The frequency device 100 can include other elements as described herein, and other elements disposed for allowing the frequency device 100 to conduct method steps as described herein. The frequency device 100 can also include other and further elements useful for interaction with the surface 120, with the user, with acoustic signals (such as emitting or detecting such signals), and otherwise.

Alternative Embodiments

After reading this application, those skilled in the art would recognize that techniques described herein, are responsive to, and transformative of, real-world data such as acoustic and vibrational signals, and resonant frequencies and impulse responses of physical devices, and provides a useful and tangible result in the service of detecting and using resonant frequencies and other information about acoustic and vibrational signals. Moreover, after reading this application, those skilled in the art would recognize that processing of acoustic and vibrational signals by a frequency device includes substantial computer control and programming, involves substantial records of acoustic signals, and involves interaction with acoustic signal hardware and optionally a user interface.

Certain aspects of the embodiments described in the present disclosure may be provided as a computer program product, or software, that may include, for example, a computer-readable storage medium or a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular embodiments. Functionality may be separated or combined in procedures differently in various embodiments of the disclosure or described with different terminology. These and other variations, modifications, additions, and improvements may fall within the scope of the disclosure as defined in the claims that follow.

The invention claimed is:

1. A method comprising:
    emitting a first acoustic signal from a first device positioned on an object;
    receiving, by the first device, one or more vibrations from the object, the vibrations being in response to the acoustic signal;
    determining a center frequency based on the vibrations received by the first device; and
    transmitting a second acoustic signal to a second device using the center frequency, the second device also positioned on the object.

2. The method of claim 1, wherein:
    the first and second acoustic signals includes an impulse response of one or more of:
    a haptic interface, a speaker.

3. The method of claim 1, further comprising:
    transmitting the second acoustic signal through the object;

receiving the second acoustic signal by the second device via the object; and determining an impulse response of the object based on a comparison between the signal received by the second device and the second acoustic signal transmitted by the first device.

4. The method of claim 3, further comprising:
adjusting operation of the first device in response to the impulse response of the object.

5. The method of claim 4, wherein:
adjusting operation include one or more of:
emitting a third acoustic signal having the center frequency near a resonant frequency of the object; or
emitting the third acoustic signal including the resonant frequency.

6. The method of claim 1, wherein:
the first device includes an electronic communication element.

7. The method of claim 6, wherein:
the first device includes a cellular telephone.

8. An apparatus including:
an object having an impulse response to an acoustic signal;
a first device positioned on the object having a resonant frequency, the first device including an acoustic signal emitter and a second signal emitter;
a second device positioned on the object, the second device including an acoustic signal receiver and a second signal receiver;
the second signal emitter and the second signal receiver being disposed to transmit and receive a signal, respectively, including information describing the acoustic signal;
one or more of the first device and the second device including a processor and instructions interpretable by the processor to determine one or more characteristics of the impulse response based on a comparison of the signal to the acoustic signal.

9. The apparatus of claim 8, wherein the first device and the second device comprise a cellular telephone.

10. The apparatus of claim 8, wherein the first device is configured to transmit an electromagnetic signal and the second device is configured to receive the electromagnetic signal.

11. The apparatus of claim 8, including instructions interpretable by the processor to determine:
an acoustic signal having a center frequency near a resonant frequency, the resonant frequency being defined in response to the impulse response.

12. The apparatus of claim 8, including instructions interpretable by the processor to determine:
an acoustic signal including a resonant frequency, the resonant frequency being defined in response to the impulse response.

13. The apparatus of claim 8, wherein:
the first device and the second device collectively include one or more of:
a haptic interface, a speaker.

14. An apparatus including:
a device acoustically coupleable to an object disposed proximate to the device, the device including:
an acoustic signal receiver;
a processor and instructions interpretable by the processor to define a plurality of user input regions with respect to a surface of the object;
the instructions interpretable by the processor to determine a particular region receiving a physical impulse, the determination based on a received acoustic signal received through the object and an impulse response of the object;
wherein the acoustic signal has a center frequency near a resonant frequency, the resonant frequency being defined in response to the impulse response;
the instructions interpretable by the processor to direct the device to perform an action associated with the particular region in response to the physical impulse.

15. The apparatus of claim 14, the acoustic signal including the resonant frequency.

16. The apparatus of claim 14, wherein:
the action associated with the particular region is responsive to a number of the physical impulses.

17. The apparatus of claim 14, wherein:
the instructions directing the device to perform an action includes instructions directing the device to emulate one or more of: a keyboard, a keypad, a mouse, a trackpad, a game controller.

18. An apparatus including:
a device acoustically coupleable to an object separate from the device, the device including:
an acoustic signal receiver;
a processor and instructions interpretable by the processor to define one or more regions with respect to a surface of the object;
the instructions interpretable by the processor to determine a particular region receiving one or more physical impulses, the determination based on a received acoustic signal received through the object and an impulse response of the object;
wherein the acoustic signal includes a resonant frequency, the resonant frequency being defined in response to the impulse response;
the instructions interpretable by the processor to direct the device to perform an action associated with the particular region in response to a number of the one or more physical impulses.

19. The apparatus of claim 18, wherein the acoustic signal has a center frequency near the resonant frequency.

20. The apparatus of as in claim 18, wherein directing the device to perform an action includes instructions directing the device to: emulate one or more of: a keyboard, a keypad, a mouse, a trackpad, a game controller.

21. A method, including steps of:
emitting a first signal from a first device, the first signal including one or more acoustic components, the first device acoustically coupled to an object having a resonant frequency;
emitting a second signal from the first device, the second signal including information describing the acoustic signal;
receiving, by a second device, the first signal and the second signal, the first signal being mediated by an impulse response of the object;
determining, by one or more of the first device and the second device, characteristics of the impulse response, based on a comparison between the first signal and the second signal.

22. The method of claim 21, further including steps of adjusting operation of one or more of: the first device, the second device, in response to the characteristics of the impulse response.

23. The method of claim 21, further including steps of:
emitting an acoustic signal from one or more of: the first device, the second device;

the acoustic signal having a center frequency near the resonant frequency; and the acoustic signal including the resonant frequency.

24. The method of claim 21, wherein one or more of: the first device, the second device, is disposed upon a surface of a medium, the medium carrying the first and second devices.

25. The method of claim 21, wherein the impulse response is a characteristic of a medium supporting the first and second devices.

26. The method of claim 21, wherein the second signal includes one or more components embedded in the first signal.

27. The method of claim 21, wherein:

the steps of emitting the first signal includes operating one or more of:

a haptic interface, a speaker.

28. The method of claim 21, wherein the second signal includes one or more electromagnetic components.

29. The method of claim 28, wherein the first device includes a cellular telephone.

* * * * *